(12) United States Patent
Norwood et al.

(10) Patent No.: US 11,337,444 B2
(45) Date of Patent: May 24, 2022

(54) RAPID HYDROLYSIS PROCESS FOR OAT-BASED BEVERAGE COMPOSITION

(71) Applicant: Jasper Products, L.L.C., Joplin, MO (US)

(72) Inventors: Eric M. Norwood, Stotts City, MO (US); Natalie L. Overfelt, Joplin, MO (US)

(73) Assignee: Jasper Products, L.L.C., Joplin, MO (US)

( * ) Notice: Subject to any disclaimer, the term of this patent is extended or adjusted under 35 U.S.C. 154(b) by 362 days.

(21) Appl. No.: 16/791,234

(22) Filed: Feb. 14, 2020

(65) Prior Publication Data

US 2020/0268022 A1    Aug. 27, 2020

Related U.S. Application Data

(60) Provisional application No. 62/809,171, filed on Feb. 22, 2019.

(51) Int. Cl.

| | | |
|---|---|---|
| A23L 2/38 | (2021.01) |
| C12P 19/02 | (2006.01) |
| C12P 19/14 | (2006.01) |
| C12P 19/12 | (2006.01) |
| A23L 7/104 | (2016.01) |
| A23L 2/56 | (2006.01) |
| A23L 29/00 | (2016.01) |
| A23L 27/40 | (2016.01) |
| A23L 29/269 | (2016.01) |
| A23L 33/115 | (2016.01) |
| A23L 33/155 | (2016.01) |
| A23L 2/60 | (2006.01) |
| A23L 2/46 | (2006.01) |

(52) U.S. Cl.
CPC ............... *A23L 2/382* (2013.01); *A23L 2/46* (2013.01); *A23L 2/56* (2013.01); *A23L 2/60* (2013.01); *A23L 7/107* (2016.08); *A23L 27/40* (2016.08); *A23L 29/015* (2016.08); *A23L 29/272* (2016.08); *A23L 33/115* (2016.08); *A23L 33/155* (2016.08); *C12P 19/02* (2013.01); *C12P 19/12* (2013.01); *C12P 19/14* (2013.01); *A23V 2002/00* (2013.01)

(58) Field of Classification Search
CPC ...... A23L 7/107; A23L 33/115; A23L 29/015; A23L 29/272; A23L 33/155; A23L 2/46; A23L 2/56; A23L 2/60; C12P 19/02; C12P 19/14; A23V 2002/00
See application file for complete search history.

(56) References Cited

U.S. PATENT DOCUMENTS 4,001,436 A * 1/1977 Clark
6,685,974 B2 * 2/2004 Whalen

FOREIGN PATENT DOCUMENTS

WO   WO 2012/174259    * 12/2012

* cited by examiner

*Primary Examiner* — Helen F Heggestad
(74) *Attorney, Agent, or Firm* — Hovey Williams LLP

(57) ABSTRACT

Rapid hydrolysis methods for producing oat-based beverage compositions, and compositions produced thereby. Continuous flow process to yield a hydrolyzed oat-based beverage in only a few hours, comprising a sequential treatment of an oat flour slurry with glucoamylase and then alpha-amylase enzyme with respective hydrolysis times of less than about 1.5 hours to yield a final hydrolyzed oat slurry, and finishing the composition with one or more flavorings or additional ingredients yield the oat-based beverage composition.

19 Claims, No Drawings

RAPID HYDROLYSIS PROCESS FOR OAT-BASED BEVERAGE COMPOSITION

CROSS-REFERENCE TO RELATED APPLICATIONS

The present application claims the priority benefit of U.S. Provisional Patent Application Ser. No. 62/809,171, filed Feb. 22, 2019, entitled RAPID HYDROLYSIS PROCESS FOR OAT-BASED BEVERAGE COMPOSITION, incorporated by reference in its entirety herein.

BACKGROUND OF THE INVENTION

Field of the Invention

The present invention relates to oat-based beverage compositions and innovative rapid hydrolysis methods of preparing the same.

Description of Related Art

There is a continuing interest in alternatives to animal milk (e.g., dairy or goat) and associated products (cheese, yogurt, etc.), with a sharp rise in recent years in plant- and nut-based "milks" including soy, rice, coconut, cashew, and almond milk. However, the nutritional value of these milk alternatives has come under scrutiny for their high added sugar and chemical additive content, along with the environmental impact of their manufacturing methods. There remains a need for improved milk alternatives, such as cereal grain based compositions. Further, there remains a need for improved processes to produce cereal grain based compositions.

SUMMARY OF THE INVENTION

Described herein are rapid hydrolysis methods for producing an oat-based beverage composition, and in particular a continuous flow process that yields a hydrolyzed oat-based beverage in only a few hours. The methods generally comprise, consist essentially, or even consist of the steps of hydrating oat flour with water in a mixer to create an oat slurry, treating the oat slurry with a glucoamylase enzyme for a first hydrolysis time (preferably less than about 1.5 hours) to hydrolyze the oat flour and yield an initial hydrolyzed oat slurry; treating the initial hydrolyzed oat slurry with an alpha-amylase enzyme for a second hydrolysis time (preferably less than about 1.5 hours) to hydrolyze the oat flour to yield a final hydrolyzed oat slurry; adding one or more of the following ingredients to the final hydrolyzed oat slurry: stabilizer, emulsifier, salt, vegetable oil, vitamins, sweetener, flavoring agent and/or buffering agent; and mixing the ingredients with said final hydrolyzed oat slurry until homogenously combined to yield said oat-based beverage composition.

Also described herein are oat-based beverage compositions produced according to the various embodiments described herein, which comprise hydrolyzed oat flour suspended in aqueous solution, wherein the hydrolyzed oat flour comprises glucoamylase and alpha-amylase hydrolysis reaction products.

DESCRIPTION OF THE INVENTION

The present invention is broadly concerned with oat-based liquid suspensions intended for consumption, which may be characterized herein as oat-based beverages, oat milk, oat drink, oat shake, drinkable meal replacer, drinkable oatmeal, and the like. The present invention is also concerned with innovative rapid starch hydrolysis processes for producing such oat-based liquid suspensions in a continuous flow process. In contrast to offline hydrolysis processes that rely on prolonged oat hydrolysis reactions in separate tanks each over a period of several (~10+) hours, the current continuous flow process with rapid hydrolysis protocol facilitates the production of a hydrolyzed oat-based beverage in less than about 5 hours total processing time, preferably less than about 3 hours total processing time as measured from the start of hydration to packaged product. It will be appreciated that this is significantly faster than existing processes that take from about 18 hours to about 36 to prepare a hydrolyzed oat formulation. In the innovated process, oat flour in aqueous suspension is hydrolyzed with selected enzymes under enhanced conditions, and mixed with one or more optional flavoring agents to yield the oat-based beverage. Advantageously, the rapid hydrolysis process can be carried out with a single tank and corresponding mixer in fluid communication with one another, and yields an oat-based beverage composition that does not require filtration and requires little to no added sugar to achieve its sweet flavor profile. As used herein the term "added sugar" means refined or "natural" sugars and syrups that are added to foods as a separate ingredient during processing or preparation, and excludes sugars naturally found or converted (e.g., through enzymatic hydrolysis of starch) in food. Total enzymatic hydrolysis time in the innovative method is less than about 5 hours, preferably less than about 3 hours, more preferably less than 2.5 hours, even more preferably less than 2 hours, and even more preferably less than 1.5 hours. In some cases, total enzymatic hydrolysis time in the innovative method can be completed in approximately 1 hour.

Oat-based beverages according to embodiments of the invention comprise hydrolyzed oat flour suspended in aqueous solution. Additional ingredients include (inactivated) amylase enzymes (preferably glucoamylase and alpha-amylase), calcium, and one or more additives, such as flavoring agents, vegetable oil(s), sweeteners, vitamins (e.g., A, D, E), stabilizers/gelation agents, emulsifiers, buffering agent(s), and/or processing aid acidifiers. Flavoring agents include one or more of salt (e.g., sea salt), cacao powder, cocoa powder, caramel, spices such as cinnamon, turmeric, chai, and natural or artificial flavor extracts including vanilla, strawberry, raspberry, blueberry, banana, coffee, pumpkin, toffee, licorice, chocolate, mocha, other seasonal flavors, and the like. Stabilizer and/or gelation agents that can be used to modify viscosity, reduce separation, and/or adjust/thicken the mouthfeel of the composition include xanthan gum, locus bean gum, gellan gum, guar gum, gelatin, pectin, carrageenan, and the like. Emulsifiers, such as DATEM/Mono Diglycerides, and/or lecithin may be included in the composition. Vegetable oils for use in some embodiments include any suitable vegetable or seed oil that remains liquid at room temperature, such as canola oil, olive oil, sunflower oil, soybean oil, corn oil, safflower oil, peanut oil, palm oil, hemp seed oil, mixtures thereof, and the like. Low-fat or no-fat embodiments are also contemplated herein comprising reduced amounts or no added vegetable oils.

One or more sweeteners or sweetening agents may be included in the oat-based beverage; however, it will be appreciated that the oat-based beverage will have some intrinsic level of sweetness from hydrolysis of the oat flour and may not require added sugars to achieve a sweet taste.

Thus, no-added sugar embodiments of the oat-based beverage composition are also contemplated herein. If desired, exemplary sweetening agents that can be added to the composition include cane sugar, stevia, maple syrup, corn syrup, molasses, agave nectar, monk fruit, as well as artificial sweeteners such as saccharin, sucralose, sugar alcohols (e.g., sorbitol, xylitol, mannitol), acesulfame potassium, aspartame, and the like. Finally, oat-based beverage compositions may include one or more buffering agent(s) and/or food grade acidifiers to adjust and maintain the pH of the composition during preparation and/or for consumption of the end product. Exemplary buffering agents include alkaline phosphates, such as potassium phosphates, and citrates, such as sodium citrate, potassium citrate, and the like. Exemplary food-grade processing aid acidifiers added to adjust the pH (and not flavor) include citric acid, maleic acid, fumaric acid, and/or phosphoric acid, among others.

TABLE

Ingredients and Amounts (when present)

| Ingredient | Approx. % wt range* |
| --- | --- |
| Oat Flour | ~7.5-11.5 |
| Acidifier | ~0.035-0.055 |
| Glucoamylase | ~0.05-0.10 |
| Alpha-amylase | ~0.01-0.09 |
| Calcium Ion Source | ~0.05-0.50 |
| Nutritional Calcium | ~0.10-0.20 |
| Buffering Agent | ~0.1-0.5 |
| Salt | ~0.01-0.09 |
| Stabilizer | ~0.01-0.05 |
| Oil | ~1.0-2.0 |
| Sweetener | ~3.0-5.0 |
| Flavoring agent (cocoa, vanilla, etc.) | ~0.5-1.5 |
| Vitamin Premix | ~0.008-0.012 |
| Water | ~80-90 (balance) |

*Based upon the total weight of the final product taken as 100% by weight.

The oat-based beverage composition is prepared by mixing oat flour and water (preferably hot water ~160° F.+/−5° F.) to create a slurry. Preferably, whole grain oat flour is used. Oats are first sized and dehulled to yield whole oat groats. The groats are then sized, toasted, and steamed, followed by grinding into a powder-like (flour) consistency. Whole grain oat flour is commercially available. Preferably, colloidal, finely milled oat flour is used. The oat flour and water slurry is then mixed on high speed (~3,600 RMP) until the oat flour is homogeneously dispersed. The pH of the slurry is then adjusted to between 5 and 6 (preferably about 5.3-5.75, more preferably about 5.4-5.7, even more preferably about 5.5) using a processing aid acidifier. The pH is selected to enhance conditions for the first enzyme addition. A glucoamylase enzyme (aka amyloglucosidase) is added to the slurry. The glucoamylase enzyme is allowed to react with the oat flour for about 15 minutes to about 1.5 hours, preferably for about 15 minutes to about 1.0 hour, and preferably from about 15 minutes to about 45 minutes, with regular agitation for hydrolysis of the oat flour to produce sugars. In this initial hydrolysis step, the glucoamylase hydrolyzes terminal (1,4)-alpha-D-glucosidic linkages successively from non-reducing ends of the oat starch to release free glucose molecules. The glucoamylase enzyme also possesses the ability to hydrolyze branched glucosidic linkages, as well as terminal (1,6)-alpha-D-glucosidic linkages in isomaltose and dextrins. Preferably, the glucoamylase is a fungal glucoamylase. Amylase AG 300 L is a preferred fungal glucoamylase, produced from a selected strain of *Aspergillus Niger.*

At the end of the first hydrolysis time, a source of nutritional calcium (e.g., calcium citrate, calcium lactate, calcium carbonate) and source of calcium ions (e.g., calcium phosphates) are added to the hydrolyzed slurry. Additional water can also be added to the slurry to increase pH and lower the temperature (to about 100-135° F.) to enhance conditions for the activity of the second enzyme. Advantageously, addition of calcium at this point in the process helps control and direct the activity of the subsequent enzyme used in the rapid hydrolysis process, as described in more detail below. An endo-acting alpha-amylase is added to the slurry and allowed to react for about 15 minutes to about 1.5 hours, preferably for about 15 minutes to about 1.0 hour, and preferably from about 15 minutes to about 45 minutes with regular agitation for further hydrolysis of the oat flour to produce additional sugars. The alpha-amylase hydrolysis step also reduces viscosity of the composition.

The calcium added during this step binds to remaining starch chains in the slurry (after the first hydrolysis), forcing the selected alpha-amylase to hydrolyze (1,4)- and (1,6)-alpha-D-glucosidic linkages at specific positions throughout the remaining starch molecules to produce maltose. Preferably, the alpha-amylase is a bacterial amylase. The selected alpha-amylase may also have side beta glucanase activity; however, it will be appreciated that use of glucoamylase as the first enzyme does not leave many linkages for the beta glucanase to act upon in the second hydrolysis. Likewise, an alpha-amylase without side beta glucanase activity can also be used to preserve more beta glucans in the final formulation if desired. BAN® 480L is a preferred endo-active alpha-amylase for use in the process. It is a bacterial amylase produced by fermentation of *Bacillus amyloliquefaciens*, with a standard strength of 480 KNU/g and thermally stable activity in the range of 158–194° F.

Notably, the first enzyme (glucoamylase) remains active after the first hydrolysis step. That is, the method does not involve a proactive step to stop this first hydrolysis reaction; however, it will be appreciated that the efficiency of the glucoamylase is reduced in the second hydrolysis step due to pH changes, among other adjustments made to the formulation to accommodate the alpha-amylase enzyme selected for the second hydrolysis step. Advantageously, because the glucoamylase remains active during the second hydrolysis step, the maltose units generated by the alpha-amylase in the second hydrolysis step are further hydrolyzed by the glucoamylase into glucose. Accordingly, it will be appreciated that the rapid hydrolysis process is able to quickly and efficiently convert a high percentage (~96%) of the oat starch into primarily glucose molecules over a period of mere hours, resulting in a pleasant and naturally sweet flavor profile in the oat-based beverage composition produced in a continuous flow process.

At the end of the second hydrolysis time, additional ingredients can be added, such as stabilizers, emulsifiers, salt, oil, buffering agents, vitamin premix, flavoring agents, and the like. The target pH is adjusted with buffering agents, if needed, to between 7.05 and 7.55. The composition is mixed until all ingredients are homogenously combined. The resulting mixture is then subjected to an Ultra High Temperature (UHT) sterilization step, which stops the first and second enzymatic reactions, and finally cooled to yield the oat-based beverage composition. The beverage composition can then be dispensed into packaging as part of the continuous flow process or may be stored in a larger tank for later packaging. In one or more embodiments, when each batch is complete, it is transferred from the batch tank to a larger holding tank that can accommodate multiple batches.

The mixture can then be subjected to direct steam injection UHT, followed by homogenization. The mixture can then be directed to an aseptic tank that feeds a bank of package fillers. In one or more embodiments, each container is in fluid communication with one another. That is, once the package filler machines start dispensing the oat beverage into packages the entire process is a continuous flow of the beverage composition from oat hydration/hydrolysis in the batch tank with mixer, to UHT, transferring, and filling/packaging, preferably with a total time of less than about 5 hours total processing time, and preferably less than about 3 hours total processing time as measured from the start of oat flour hydration to packaged product.

Thus, embodiments described here rely on sequential hydrolysis of oat starches, first with a glucoamylase and then with an alpha-amylase (with ongoing hydrolysis by the glucoamylase). Thus, enzymes used in the process preferably consist of glucoamylase and alpha-amylase added in sequential order. In one or more embodiments, the process of preparing the inventive oat-based beverage does not involve the introduction of any other enzymes for oat starch hydrolysis, and more specifically the process excludes any protease, cellulase, glucanase (except the noted alpha-amylase with side beta glucanase activity), and/or beta-amylase enzymes being introduced into the composition.

Using the foregoing information, different oat-based beverage compositions can be prepared using a continuous flow, rapid hydrolysis process, including full fat original oat beverages with or without added sugars, low fat oat beverages with or without added sugars, no added sugar oat beverages, and flavored versions thereof (e.g., vanilla, chocolate, strawberry, etc.). The compositions generally have a protein content of about 3 g+/−10 wt % per 240 mL serving. Embodiments of the invention are preferably free of trans fats, and relatively low in fat content. For example, the full fat version comprises about 5 g of fat+/−10 wt % per 240 mL serving. Fats present in the compositions are primary monounsaturated and polyunsaturated fats, with small relative amounts of saturated fats. Among fatty acids, the compositions preferably comprise primarily healthy fats, such as omega-6 (linoleic>15%) and omega-9 fatty acids (Oleic>70%), with the remainder being palmitic acid (<9%) and stearic acid (<5%). Added sugar versions preferably comprise less than about 11 g of added sugar+/−10 wt % per 240 mL serving. The sugar profile of the compositions is primarily in form of glucose (>95% of total sugars) and small amounts of maltose (~3%-4% of total sugars). The compositions contain very low (or no) levels of lactose<0.1%, low sucrose<0.1%, and low fructose<0.1%. The compositions have pleasant mouthfeel and taste, with a Brookfield Viscosity from about 20 to about 35 cP, more preferably from about 25 to about 30 cP, and even more preferably about 27 cP at 50° F. (100 rpm).

The oat-based beverage compositions of the invention can be used as a substitute for dairy milk or other animal milks (e.g., goat), and are improved over other dairy alternatives, such as plant or nut milks. In one or more embodiments, the oat-based beverage composition may be substantially free of one or more allergenic ingredients, including dairy, nuts, soy, gluten, egg, and/or dairy-, nut-, soy-, gluten-, and/or egg-derived ingredients. As used herein, "substantially free" means that the ingredient or component is not intentionally added as an ingredient in the composition, although incidental amounts may be present as impurities, etc. In some embodiments, the composition or individual ingredients can be (or may already have been) further purified or treated to remove even trace amounts of one or more allergenic ingredients, such that the composition could be designated as "allergen free." The oat-based beverage composition can be packaged for consumption or used as an ingredient in other food preparations. For example, the composition can be consumed directly as a beverage, or used on breakfast cereal, as a coffee or tea creamer, in baked goods, and the like. It can also be supplemented or mixed with a source of protein, such as a protein powder (e.g., milk proteins or vegetable proteins), to create a protein shake.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

No Added Sugar Oat Beverage

| Ingredient | % wt* |
| --- | --- |
| Oat Whole Flour Low Viscosity OLV61 | 9.3152 |
| Amylase AG 300L glucoamylase (Novozymes ®) | 0.0931 |
| BAN ® 480 L alpha-amylase (Novozymes ®) with side beta-glucanase activity | 0.0465 |
| Calcium TCP (Tricalcium phosphate) | 0.2911 |
| Calcium Carbonate (CalEssence 70) | 0.1455 |
| Dipotassium Phosphate, Anhydrous (DKP) | 0.3493 |
| Sodium Chloride (Sea Salt) | 0.0582 |
| Gellan Gum (KELCOGEL ® HA-B) | 0.0291 |
| Oil, Sunflower Hi Oleic | 1.4555 |
| Vitamin Premix (A, D, E) | 0.01 |
| Water | ~88.21 (balance) |

*Based upon the total weight of the final product taken as 100% by weight.

An oat beverage was made using the above ingredients and the following continuous flow process using the inventive rapid hydrolysis protocol:

Pull 75% of total formulation water at 160±5° F. and maintain circulation in system between the high shear mixer and batch tank. Add the whole grain oat flour to the mixer to begin hydrating. After adding the oat flour, adjust the batch pH to a target of 5.5 using a small amount of phosphoric acid (ProcAid, Acid, Phosphoric 85%). Slowly add Amylase AG 300L (glucoamylase), push to batch tank, and start a 45-minute hydrolysis timer on the batch. Amylase AG 300L, hydrolyzes (1,4)- and (1,6)-alpha-D-glucosidic linkages at the non-reducing ends of the oat starch, as well as branched glucosidic linkages.

After the 45-minute hydrolysis, add the remaining amount of formulation water at ambient temperature to increase the pH and decrease the temperature of the batch, optimizing conditions for the activity of the second enzyme, BAN 480 L (alpha-amylase enzyme). Maintain the overall batch temperature range between 100 and 135° F.

Add the calcium carbonate and tricalcium phosphate to the high shear mixer to control activity of BAN 480 L. Next, slowly add BAN 480 L and start a 45-minute hydrolysis timer on the batch. BAN 480 L is added to hydrolyze (1,4)-alpha-D-glucosidic linkages in oat starch, which is used to improve product viscosity and results in the production of maltose. The resulting maltose units are further hydrolyzed into glucose by the Amylase AG 300 L remaining in the formulation. The reactions involving Amylase AG 300 L and BAN 480 L are allowed to continue for 45 minutes with regular agitation before the next step.

After the second 45 minute hydrolysis, add gellan gum, sea salt, dipotassium phosphate, vitamin premix, and sunflower oil. Mix for ten minutes and pull a lab testing sample.

Record pH, % total solids and Quality Control release time. Transfer batch to raw surge tank with agitation, and cool to <40° F. Subject the formulation to ultra-high temperature (UHT) processing to stop the enzymatic reactions and sterilize the formulation. Homogenize at 3,500 psi after sterilization. Set homogenizer 2nd stage at 500 psi, then set 1st stage at 3,000 psi. Continuously agitate in the sterile "A-Tank." Final product details are in the table below.

Oat Beverage Final Product

| Specifications per serving size (240 mL) | Value |
|---|---|
| pH | 7.34 |
| Viscosity* | 27.4 cp |
| Total Fat | 2.4 g |
| Saturated Fat | 0.48 g |
| Monounsaturated Fat | 2.9 g |
| Polyunsaturated Fat | 0.67 g |
| Trans Fat | 0 g |
| Total Dietary Fiber | 1.6% |
| Beta-Glucan | 0.12% |
| Total Sugar | 10.8 g |
| Galactose | <0.1% |
| Fructose | <0.1% |
| Glucose | 10.4 g |
| Sucrose | <0.1% |
| Maltose | 0.39 g |
| Lactose | <0.1% |

*As measured with a Brookfield Viscometer (S-61 spindle, 100 RPM, 46%, 9.5° C.)

Example 2

Low Fat Oat Beverage

| Ingredient | % wt* |
|---|---|
| Oat Whole Flour Low Viscosity OLV61 | 9.3050 |
| Amylase AG 300L glucoamylase (Novozymes ®) | 0.0930 |
| BAN ® 480 L alpha-amylase (Novozymes ®) | 0.0465 |
| Calcium TCP (Tricalcium phosphate) | 0.2908 |
| Calcium Carbonate (CalEssence 70) | 0.1454 |
| Dipotassium Phosphate, Anhydrous (DKP) | 0.3489 |
| Sodium Chloride (Sea Salt) | 0.0582 |
| Gellan Gum (KELCOGEL ® HA-B) | 0.0291 |
| Vitamin Premix (A, D, E) | 0.01 |
| Water | ~89.67 (balance) |

*Based upon the total weight of the final product taken as 100% by weight.

An oat beverage was made using the above ingredients and the rapid hydrolysis process described in Example 1, except that sunflower oil was not added to the composition, to yield a low-fat oat beverage.

Example 3

Chocolate Oat Beverage

| Ingredient | % wt* |
|---|---|
| Oat Whole Flour Low Viscosity OLV61 | 9.1634 |
| Cocoa powder (Alkalized, 10-12% SIENNA, Cargill ®) | 0.5040 |
| Cocoa powder (high fat with alkali, 22-24% ARISTOCRAT, Cargill ®) | 0.5040 |
| Amylase AG 300L glucoamylase (Novozymes ®) | 0.0915 |
| BAN ® 480L alpha-amylase (Novozymes ®) | 0.0458 |
| Calcium TCP (Tricalcium phosphate) | 0.2864 |
| Calcium Carbonate (CalEssence 70) | 0.1432 |
| Dipotassium Phosphate, Anhydrous (DKP) | 0.3436 |
| Sodium Chloride (Sea Salt) | 0.0573 |
| Gellan Gum (KELCOGEL ® HA-B) | 0.0286 |
| Oil, Sunflower Hi Oleic | 1.4318 |
| Liquid Cane Sugar (Missouri Sugars) | 4.5817 |
| Vanilla, natural flavoring (Flavorchem ®) | 0.0172 |
| Vitamin Premix (A, D, E) | 0.01 |
| Water | ~88.21 (balance) |

*Based upon the total weight of the final product taken as 100% by weight.

An oat beverage was made using the above ingredients and a rapid hydrolysis process similar to that described in Example 1, except that the cocoa powder was added along with the oats in the mixing tank for hydration before adding the enzymes. In addition, cane sugar was added along with the sunflower oil, followed by vanilla flavoring before the final mixing step. The resulting chocolate oat beverage had 8 grams of added sugar per 240 mL serving.

Example 4

No Added Sugar Oat Beverage 2

| Ingredient | % wt* |
|---|---|
| Oat Whole Flour Low Viscosity OLV61 | 9.3152 |
| Amylase AG 300L glucoamylase (Novozymes ®) | 0.0931 |
| BAN ® 480 LS alpha-amylase (Novozymes ®) | 0.0465 |
| Calcium TCP (Tricalcium phosphate) | 0.2911 |

-continued

| Ingredient | % wt* |
|---|---|
| Calcium Carbonate (CalEssence 70) | 0.1455 |
| Dipotassium Phosphate, Anhydrous (DKP) | 0.3493 |
| Sodium Chloride (Sea Salt) | 0.0582 |
| Gellan Gum (KELCOGEL ® HA-B) | 0.0291 |
| Oil, Sunflower Hi Oleic | 1.4555 |
| Vitamin Premix (A, D, E) | 0.01 |
| Water | ~88.20 (balance) |

*Based upon the total weight of the final product taken as 100% by weight.

An oat beverage was made using the above ingredients and the rapid hydrolysis process described in Example 1, except that a different alpha amylase was used to preserve beta-glucans present in the whole oat flour.

Oat Beverage Final Product

| Specifications per serving size (240 mL) | Value |
|---|---|
| Beta-Glucan | 0.28% |
| Total Sugar | 10.4 g |
| Galactose | <0.1% |
| Fructose | <0.1% |
| Glucose | 9.9 g |
| Sucrose | <0.1% |
| Maltose | 0.53 g |
| Lactose | <0.1% |

Example 5

No Added Sugar Original Oat Beverage 3

| Ingredient | %wt* |
|---|---|
| Oat Flour Whole Colloidal Fine MPF M09** | 8.7464 |
| Amylase AG 300L glucoamylase (Novozymes ®) | 0.0932 |
| BAN ® 480 L alpha-amylase (Novozymes ®) | 0.0466 |
| Calcium TCP (Tricalcium phosphate) | 0.2915 |
| Calcium Carbonate (CalEssence 70) | 0.1458 |
| Dipotassium Phosphate, Anhydrous (DKP) | 0.3499 |
| Sodium Chloride (Sea Salt) | 0.0583 |
| Gellan Gum (KELCOGEL ® HA-B) | 0.0292 |
| Oil, Sunflower Hi Oleic | 1.4577 |
| Vitamin Premix (A, D, E) | 0.0035 |
| Water | ~88.73 (balance) |

*Based upon the total weight of the final product taken as 100% by weight.
**Finely milled, 5-15% 200 mesh An oat beverage was made using the above ingredients and the following continuous flow process using a further shortened rapid hydrolysis protocol:

Pull 75% of total formulation water at 160±5° F. and maintain circulation in system between the high shear mixer and batch tank. Add the whole grain colloidal oat flour to the mixer to begin hydrating. After adding the oat flour, adjust the batch pH to a target of 5.5 (acceptable range 5.3-5.7) using a small amount of phosphoric acid (ProcAid, Acid, Phosphoric 85%) slowly added (approx. 0.0437% wt). Slowly add Amylase AG 300L (glucoamylase), push to batch tank, and start a 30-minute hydrolysis timer on the batch. Amylase AG 300L, hydrolyzes (1,4)- and (1,6)-alpha-D-glucosidic linkages at the non-reducing ends of the oat starch, as well as branched glucosidic linkages.

After the 30-minute hydrolysis, add the remaining amount of formulation water at ambient temperature to increase the pH and decrease the temperature of the batch, for the second enzyme, BAN 480 L (alpha-amylase enzyme). Maintain the overall batch temperature range between 100 and 135° F.

First, add the calcium carbonate and tricalcium phosphate to the high shear mixer. Next, slowly add BAN 480 L and start a 30-minute hydrolysis timer on the batch. BAN 480 L is added to hydrolyze (1,4)-alpha-D-glucosidic linkages in oat starch, which is used to improve product viscosity and results in the production of maltose. The resulting maltose units are further hydrolyzed into glucose by the ongoing activity of Amylase AG 300 L remaining in the formulation. The reactions involving Amylase AG 300 L and BAN 480 L are allowed to continue with regular agitation before the next step.

After the second 30-minute hydrolysis, add gellan gum, sea salt, dipotassium phosphate, vitamin premix, and sunflower oil. Mix for ten minutes and pull a lab testing sample.

Record pH, % total solids and Quality Control release time. Transfer batch to raw surge tank with agitation, and cool to <40° F. Subject the formulation to ultra-high temperature (UHT) processing to stop the enzymatic reactions and sterilize the formulation. Homogenize at 3,500 psi after sterilization. Set homogenizer 2nd stage at 500 psi, then set 1st stage at 3,000 psi. Continuously agitate in the sterile "A-Tank."

Example 6

No Added Sugar Vanilla Oat Beverage

| Ingredient | % wt* |
|---|---|
| Oat Flour Whole Colloidal Fine MPF M09** | 7.8897 |
| Amylase AG 300L glucoamylase (Novozymes ®) | 0.0934 |
| BAN ® 480 L alpha-amylase (Novozymes ®) | 0.0467 |
| Calcium TCP (Tricalcium phosphate) | 0.2922 |
| Calcium Carbonate (CalEssence 70) | 0.1461 |
| Dipotassium Phosphate, Anhydrous (DKP) | 0.3507 |
| Sodium Chloride (Sea Salt) | 0.0584 |
| Gellan Gum (KELCOGEL ® HA-B) | 0.0292 |
| Stevia extract (TASETVA ®) | 0.0024 |
| Oil, Sunflower Hi Oleic | 1.4611 |
| Vanilla, natural flavoring (FLAVORCHEM ®) | 0.2495 |
| Vitamin Premix (A, D, E) | 0.0035 |
| Water | ~89.33 (balance) |

*Based upon the total weight of the final product taken as 100% by weight.
**Finely milled, 5-15% 200 mesh An oat beverage was made using the above ingredients and a rapid hydrolysis process similar to that described in Example 5, except that the Stevia extract was added along with the sunflower oil, followed by vanilla flavoring before the final mixing step.

Example 7

Chocolate Oat Beverage

| Ingredient | % wt* |
|---|---|
| Oat Flour Whole Colloidal Fine MPF M09** | 9.2586 |
| Cocoa powder (Alkalized, 10-12% SIENNA, Cargill ®) | 0.5092 |
| Cocoa powder (high fat with alkali, 22-24% ARISTOCRAT, Cargill ®) | 0.5092 |
| Amylase AG 300L glucoamylase (Novozymes ®) | 0.0925 |
| BAN ® 480 L alpha-amylase (Novozymes ®) | 0.0462 |
| Calcium TCP (Tricalcium phosphate) | 0.2893 |

-continued

| Ingredient | % wt* |
| --- | --- |
| Calcium Carbonate (CalEssence 70) | 0.1447 |
| Dipotassium Phosphate, Anhydrous (DKP) | 0.3472 |
| Sodium Chloride (Sea Salt) | 0.0579 |
| Gellan Gum (KELCOGEL ® HA-B) | 0.0289 |
| Oil, Sunflower Hi Oleic | 1.4611 |
| Stevia extract (TASETVA ®) | 0.0025 |
| Sucrose (liquid cane sugar) | 0.3472 |
| Flavoring, sweetness enhancer | 0.1201 |
| Chocolate, natural flavoring | 0.1042 |
| Vanilla, natural flavoring (FLAVORCHEM ®) | 0.0174 |
| Vitamin Premix (A, D, E) | 0.0035 |
| Water | ~86.6 (balance) |

*Based upon the total weight of the final product taken as 100% by weight.
**Finely milled, 5-15% 200 mesh An oat beverage was made using the above ingredients and a rapid hydrolysis process similar to that described in Example 5, except that cocoa powder was added along with the oats in the mixing tank for hydration before adding the enzymes. In addition, cane sugar and stevia were added along with the sunflower oil, followed by natural flavorings before the final mixing step. The resulting chocolate oat beverage had <1 grams of added (cane) sugar per 240 mL serving, excluding naturally occurring sugars from the converted oat flour.

The invention claimed is:

1. A rapid hydrolysis method for producing an oat-based beverage composition, said method comprising:
   (a) hydrating oat flour with water in a mixer to create an oat slurry;
   (b) treating said oat slurry with a glucoamylase enzyme for a first hydrolysis time to hydrolyze said oat flour and yield an initial hydrolyzed oat slurry;
   (c) treating said initial hydrolyzed oat slurry produced in step (b) with an alpha-amylase enzyme for a second hydrolysis time to hydrolyze said oat flour to yield a final hydrolyzed oat slurry; and
   (d) mixing one or more of the following ingredients with said final hydrolyzed oat slurry: stabilizer, emulsifier, salt, vegetable oil, vitamins, sweetener, flavoring agent and/or buffering agent, until homogenously combined to yield said oat-based beverage composition.

2. The method of claim 1, wherein said oat flour is a colloidal whole grain oat flour.

3. The method of claim 1, further comprising adjusting the pH of said oat slurry to between 5 and 6 before said treating (b) with glucoamylase.

4. The method of claim 1, wherein said first hydrolysis time lasts for about 15 minutes to about 1.5 hours.

5. The method of claim 1, further comprising adding a source of nutritional calcium and source of calcium ions to said initial hydrolyzed oat slurry produced in step (b) before said treating (c) with said alpha-amylase.

6. The method of claim 1, wherein said second hydrolysis time lasts for about 15 minutes to about 1.5 hours.

7. The method of claim 1, wherein said steps (a)-(d) are carried out as a continuous flow process.

8. The method of claim 1, wherein said oat-based beverage composition is chocolate flavored, said method further comprising adding cocoa powder to said oat slurry during said hydration step (a).

9. The method of claim 1, wherein said first and second hydrolysis times are carried out for a total hydrolysis time of less than 3 hours.

10. The method of claim 1, wherein the enzymes used in said method consist of glucoamylase and alpha-amylase.

11. The method of claim 1, wherein said the enzymes used in said method exclude the addition of proteinase, cellulase, glucanase, and/or beta-amylase enzymes.

12. The method of claim 1, wherein said glucoamylase is a fungal glucoamylase that hydrolyzes terminal (1,4)-alpha-D-glucosidic linkages successively from non-reducing ends of the oat starch to release glucose molecules, and hydrolyzes terminal (1,6)-alpha-D-glucosidic linkages in isomaltose and dextrins in said initial hydrolyzed oat slurry.

13. The method of claim 1, wherein said alpha-amylase is a bacterial amylase that hydrolyzes (1,4)-alpha-D-glucosidic and (1,6)-alpha-D-glucosidic linkages at specific points producing maltose in said final hydrolyzed oat slurry.

14. The method of claim 13, wherein said maltose is further hydrolyzed into glucose by said glucoamylase during said second hydrolysis step to yield said final hydrolyzed oat slurry.

15. The method of claim 1, wherein said oat-based beverage composition is produced in less than 5 hours.

16. The method of claim 1, wherein said steps (a)-(d) are carried out with a single tank and corresponding mixer in fluid communication.

17. The method of claim 1, wherein a filtration step is not required during any of steps (a)-(d) to yield said oat-based beverage composition.

18. The method of claim 1, further comprising (e) subjecting the mixture of said ingredients and final hydrolyzed oat slurry to Ultra High Temperature (UHT) sterilization and cooling to yield said oat-based beverage composition.

19. The method of claim 18, further comprising (f) dispensing said oat-based beverage composition into consumer packaging, wherein said oat-based beverage composition is produced in less than about 5 hours measured from said hydrating step (a) through said dispensing step (f).

* * * * *